(12) United States Patent
Zolli (10) Patent No.: US 9,795,770 B1
(45) Date of Patent: Oct. 24, 2017

(54) BENDABLE NASAL AIRWAY TUBE DEVICE AND METHOD OF BENDING SAME

(71) Applicant: Christine Lydie Zolli, Oldwick, NJ (US)

(72) Inventor: Christine Lydie Zolli, Oldwick, NJ (US)

( * ) Notice: Subject to any disclaimer, the term of this patent is extended or adjusted under 35 U.S.C. 154(b) by 0 days.

(21) Appl. No.: 15/218,380

(22) Filed: Jul. 25, 2016

(51) Int. Cl.
| | | |
|---|---|---|
| *A61F 5/04* | (2006.01) |
| *A61M 29/00* | (2006.01) |
| *A61M 16/06* | (2006.01) |
| *A61M 16/08* | (2006.01) |

(52) U.S. Cl.
CPC ........ *A61M 29/00* (2013.01); *A61M 16/0672* (2014.02); *A61M 16/0816* (2013.01); *A61M 2210/0618* (2013.01)

(58) Field of Classification Search
CPC ................. A61F 5/04; A61F 5/05; A61F 5/08
USPC ....... 606/196, 199; 128/83, 87, 89, 270, 325
See application file for complete search history.

(56) References Cited

U.S. PATENT DOCUMENTS 8,517,729 B2 * 8/2013 Martin ................. A61J 7/0061
433/80

* cited by examiner

*Primary Examiner* — Vy Bui
(74) *Attorney, Agent, or Firm* — Robert J. Hess; Hess Patent Law Firm (57) ABSTRACT

A nasal airway passage device that keeps a nasal airway passage open when inserted into both nostrils. The device includes a hollow body having two hollow legs and a transverse segment that has a central opening. A malleable wire is embedded within a wall of the body, that is, embedded in a wall of each of the legs and embedded a wall of the transverse segment. The wire helps to retain the legs in either a straight orientation or a curved orientation. A band may be provided that encircles the legs initially and moves to encircle the transverse segment upon insertion of the legs into the nostrils.

12 Claims, 10 Drawing Sheets

BENDABLE NASAL AIRWAY TUBE DEVICE AND METHOD OF BENDING SAME

BACKGROUND OF THE INVENTION

Field of the Invention

The invention relates to a nasal airway passage device that prevents drag going into the nasal cavity and does not scratch the lining of the nose.

Discussion of Related Art

US Patent No. 20060272640 mentions in effect that:

We have all had occasion, at some point in our lives, to experiment the discomfort of a stuffed nose. Doubtless there exists an instinctive desire to breathe through one's nose. Attempting, when one's nose is blocked, to overcome the resistance put up by the nasal passages against the movement of air is associated with a feeling of general discomfort and tiredness. The normal functioning of the entire respiratory system depends on adequate nasal permeability.

A nasal obstruction is a situation in which a sufficient quantity of air does not reach the lungs upon breathing exclusively through one's nose. A nasal obstruction is either due to a disorder in the functioning of erectile structures, located within the nasal cavities and called nasal concha, within which should be considered inflammations of nasal mucosa provoked by allergies, medication, irritating substances, infections, etc., or to a disorder of the anatomical structures of the nose, both within (nasal cavity and nasal wall), and without (nasal cone).

A nasal strip dilator can "provide benefits to persons who suffer from slight snoring and objective nasal obstruction, caused by seasonal allergies or rhinitis, although those who suffer severe apneas or have a very large nose will probably not notice the difference if they use the dilator". Likewise, pregnant women in the final months of gestation can also benefit from dilators. The usefulness of dilators is just one factor among many others that are combined in the remission of snoring, such as a careful diet, not being overweight, tobacco or alcohol, especially before going to sleep. This method is palliative for relief of slight snoring, and should not be considered to be a solution for more severe problems such as apnea.

Such a solution lies in substantially improving breathing with an inhaler device in cases in which the affected person should have an anatomical, morphological and physiological condition of the nose itself, smoking habits, winter pathologies, etc. that may bring about a ventilation insufficiency of the nasal cavities. This implicates compensating the respiratory function by breathing through the mouth, motivating disorders such as mouth dryness, night snoring, sleep disorders, etc.

U.S. Pat. No. 3,935,859 discloses a one piece plastic splint presized to fit the nasal cavities. According to this patent:

The splint limbs or elements for the nostrils are joined at an isthmus that embraces the columella. This provides an anterior anchor or fixation without the necessity of sutures. Furthermore, the isthmus positively prevents the potentially fatal aspiration that might otherwise occur by dislodgement of an anterior suture. A deeply placed posterior suture provides a second spaced fixation.

The splint limbs or elements each have a breathing passage that remains unoccluded as nasal packing is added. The presized splints have rounded edges that provide maximum comfort under the circumstances. However, the plastic material yet can be cut if special contour is required at the time of surgery.

The splint stabilized the septum and surrounding tissues and provides immobilization during healing. When properly placed, the danger of hematoma formation is virtually eliminated. The breathing passages, if clogged, are easily cleaned by aspiration or other simple procedures.

The following italicized paragraphs are excerpts are under Copyright © 2011 The Kotler Nasal Airway as set forth on webpages at http://www.nasalairway.com/the—need.php, http://www.kotlernasalairway.com/instructions-use.php and http://www.kotlernasalairway.com/components-described.php mention:

Today, it is common knowledge among the lay public that nasal and/or sinus surgery requires packing. But, for good reason, packing has had "bad press" for decades. For some, the lack of normal nasal air flow induces anxiety, claustrophobia. The obligatory mouth-breathing causes a dry throat and discomfort. The breath can become unsavory, malodorous. Smell, critical to the enjoyment of food, is compromised. "It's no fun" is the common refrain.

Kotler Nasal Airway™ is used to provide the post-nasal and/or sinus surgery patient a patent nasal airway despite the nose being packed or filled by any liquids. The device also provides the anesthesiologist access to suction the pharynx following completion of surgical procedure.

The Kotler Nasal Airway™ kit consists of.

The latex-free, medical-grade silicone double nasal airway connected by a bridge.

A standard flexible 10Fr suction catheter.

A 3 cc Luer-Lok syringe and syringe adapter tip.

The double-tube airway device and the suction catheter are for use in surgery. The syringe and tip are for post-operative irrigation.

For ease of insertion, the tubes can be lubricated with saline, ointment, or lubricating jelly. After initial, partial insertion, using a standard, thin-tip nasal speculum, inspect the nasal interior to ascertain the position of the airways within the nasal cavity.

Under direct vision, advance the airways further into the nose. Next, using the inferior speculum blade or a bayonet forceps, direct each airway downward onto the floor.

The tube will snap into place onto the floor of the nose and maintain that position, lateral to the pre-maxillary bone and medial to the inferior turbinate.

When both nasal tubes are properly seated, the bridge connecting the two will be flush against the columella.

Note: If an open procedure has been performed, the surgeon may wish to divide the bridge and secure each tube separately, rather than have the bridge contact the transcolumellar incision.

The "back openings" of the tubes sit at the posterior nasal passageway, beyond the area of packing, yet not abutting the back wall of the nasopharynx.

After insertion and seating of the nasal airway, the surgeon passes the 10Fr plastic suction catheter through each tube and suctions fluids from the pharynx. This maneuver also confirms that the back opening of the device is unobstructed.

Later, the anesthesia specialist, using the same flexible suction catheter, will avail himself of this direct pathway to the pharynx for suctioning blood and mucous from throat.

While the packing of choice or gel is placed, the nasal speculum stabilizes the airway tube.

A standard 10Fr plastic suction catheter is another kit component. After insertion and seating of the nasal airway, the surgeon passes the catheter through each tube and suctions fluids from the pharynx. This maneuver confirms that tube placement is satisfactory, that there is no obstructing of the back opening of the device.

Later, the anesthesia specialist, using the same flexible suction catheter, will happily avail himself of this direct pathway to the pharynx for suctioning blood and mucous from throat. This avoids the typical struggle with the awakening patient, as the anesthesia specialist seeks to traverse the oral pharynx to withdraw fluids from the throat just prior to removing the oral endotracheal tube or laryngeal mask.

Also supplied are a standard 3 cc Luer-Lok syringe with a "Christmas tree" irrigating tip for home irrigation of the tubes' lumens to relieve any clogging by mucous or blood.

The airway may remain in place consistent with clinical need. The device easily slides out by grasping the wall of either tube or both tubes with a clamp or forceps. Anesthetizing and shrinking the nasal mucosa with a topical anesthetic and decongestant combination, prior to removal of airway and packing, provides a smooth and comfortable patient experience.

The following italicized paragraphs are taken from the webpage at http://www.alaxo.com/alaxolito_eng.html:

The AlaxoLito Nasal Stent is a medical device for treatment of decreased nasal breathing as well as resulting snoring. Causes can be nasal alar collapse, nasal valve collapse or turbinate hyperplasia.

There are two different product variants which splint either the anterior nasal cavity only [AlaxoLito Nasal Stent] or the full length nasal passage [AlaxoLito Plus Nasal Stent].

Figure 1:
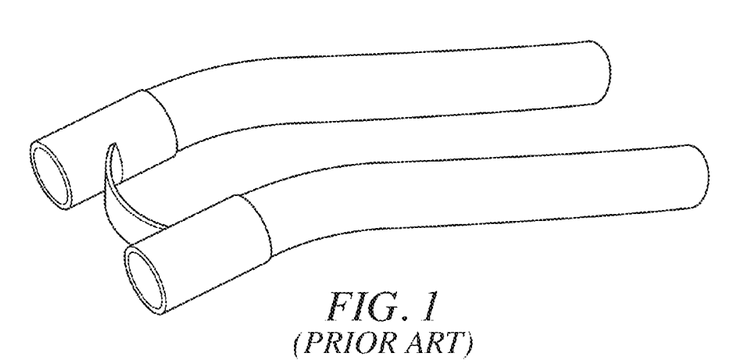
FIG. 1 is an isometric view of a conventional nasal airway tube that is commercialized under the last name of Robert Kotler, MD, FACS.
Figure 2:
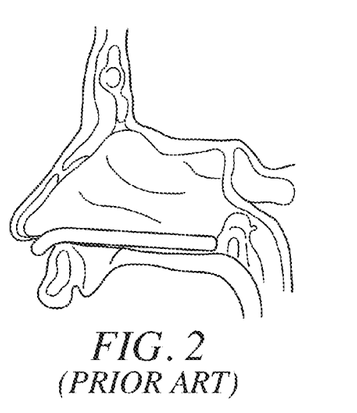
FIG. 2 is a schematic illustration of the conventional nasal airway tube of FIG. 1 that is nesting on a floor of a nasal passage.
Figure 3:
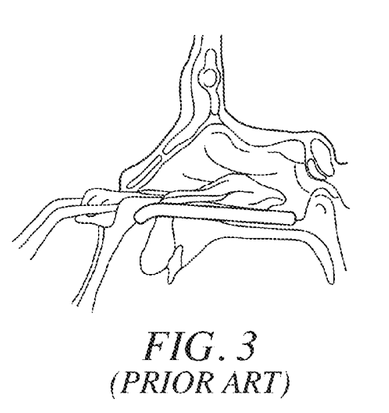
FIG. 3 is a schematic illustration of the conventional nasal airway tube of FIG. 1 after being in the position of FIG. 2, but shown with packing inserted as the airway is retracted by a thin nasal speculum.
Figure 4:
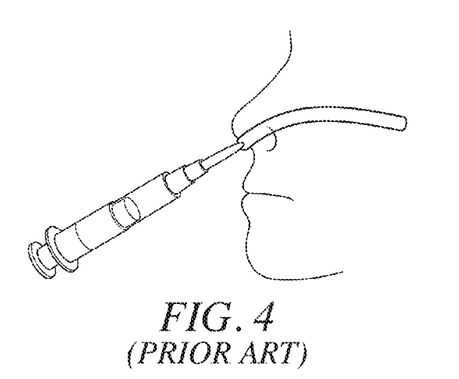
FIG. 4 is a schematic illustration of the conventional nasal airway tube of FIG. 1 after being in the position of FIG. 2, but shown in use during a post-operative period during which irrigation of the tubes' lumena will relieve any clogging by mucous or blood.
Figure 5:
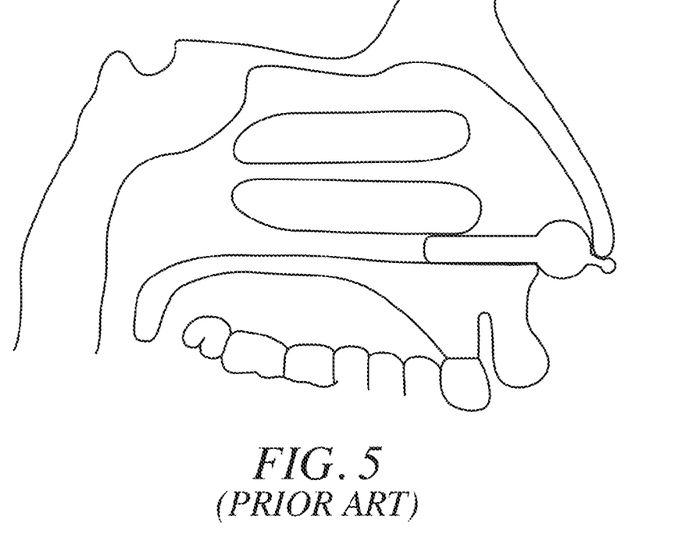
FIG. 5 is a schematic diagram to show positioning of a conventional nasal stent in an anterior nasal cavity that is sized to splint the anterior nasal cavity only.
Figure 6:
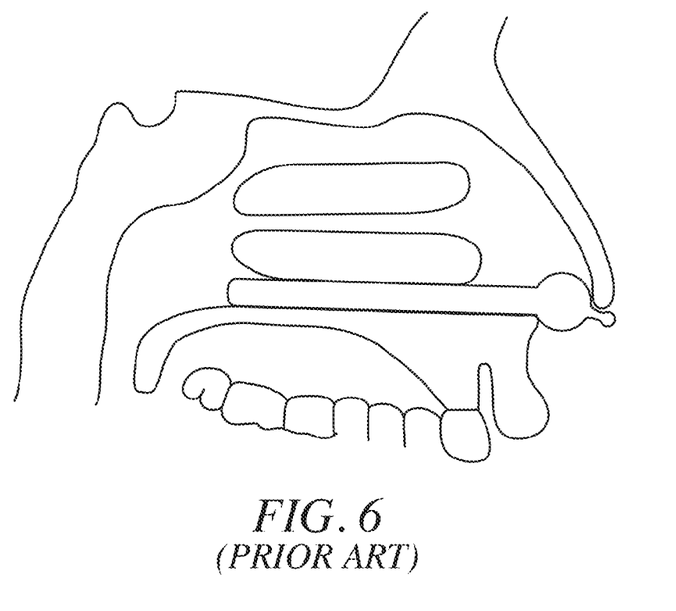
FIG. 6 is a schematic diagram to show positioning of a conventional nasal stent in an anterior nasal cavity that is sized to splint the full length nasal cavity a part of which is the anterior nasal cavity.

The smooth stent braid is made from the memory metal nitinol. It has a ball-shaped widening which is positioned at the nasal valve and a cylindrical longer section which splints the turbinates. The—two stents of FIGS. 5 and 6 are—self-applied to the nose by the patient, usually for the period of sleep or e.g. during sports activities.

The stent has an opening force adapted to supporting the nasal alar and nasal valve and to splinting of the turbinates. Thereby a healthy diameter of the airway and a very good therapeutic effect are achieved concurrent with high wearing comfort. The nasal tissue is not overstretched and no mucosal irritation occurs.

The innovative concept of the AlaxoLito Nasal Stent for the first time enables an efficient conservative therapy of nasal alar collapse and turbinate hyperplasia. As a result wellness and health of a large number of patients can be improved.

For application the AlaxoLito Nasal Stent is pulled into a thin introduction tube, which then is introduced horizontally into the nose (in the lower or middle nasal passage). Subsequent retraction of the introduction tube from the nose leads to self-expansion of the nitinol braid. The ball-shaped widening locates directly at the nasal valve. The cylindrical section splints the anterior (AlaxoLito) or the full (AlaxoLito Pus), resp., nasal passage. Usually each one stent is introduced into the right and the left nostril. Simple handling of the AlaxoLito Nasal Stent allows easy self-application by the patient.

The nasal stent is optimized in its design so that it is hardly visible in the nostril.

It is desired to provide a nasal device that will not injure blood vessels within the nose upon insertion and that retains in position within the nose and is easily removed.

SUMMARY OF THE INVENTION

The present invention relates to a nasal airway passage device that keeps a nasal airway passage open when inserted into both nostrils. The device includes a hollow body having two hollow legs and a hollow transverse segment that has a central opening. The legs extend from the transverse segment. A malleable wire is embedded within a wall of the body, that is, embedded in a wall of each of the legs and embedded a wall of the transverse segment.

At least the legs of the body are made of a bendable material that bends in unison with bending of the malleable wire between a substantially straight orientation and a curved orientation. The malleable wire retains the legs in the substantially straight orientation in an absence of a manual bending force that tends to move the legs and wire out of the substantially straight orientation. The malleable wire retains the legs in the curved orientation in an absence of a manual bending force that tends to move the legs and wire out of the curved orientation.

A band may be provided that starts out encircling both of the legs and is pushed under manual force exerted by the nose to encircle the transverse segment.

BRIEF DESCRIPTION OF THE DRAWING

For a better understanding of the present invention, reference is made to the following description and accompanying drawings, while the scope of the invention is set forth in the appended claims.

DESCRIPTION OF THE PREFERRED EMBODIMENT

Turning to the figures, FIGS. 1-4 show a nasal airway tube commercialized under the last name of Robert Kotler, MD, FACS. As can be appreciated from the figures and from the description of this nasal airway tube in the Background of the Invention, its intended use after rhinoplasty surgery surrounded by nasal packing. Post-operative care involves the use of a catheter inserted into the proximal open end of the nasal airway tube to suction fluids from the pharynx. A clamp or forceps are mentioned to be used to effect removal of the nasal airway tube.

FIG. 5 and FIG. 6 show nasal stents commercialized by Alaxo GmbH that are self-applied to the nose by the patient.

Figure 7:
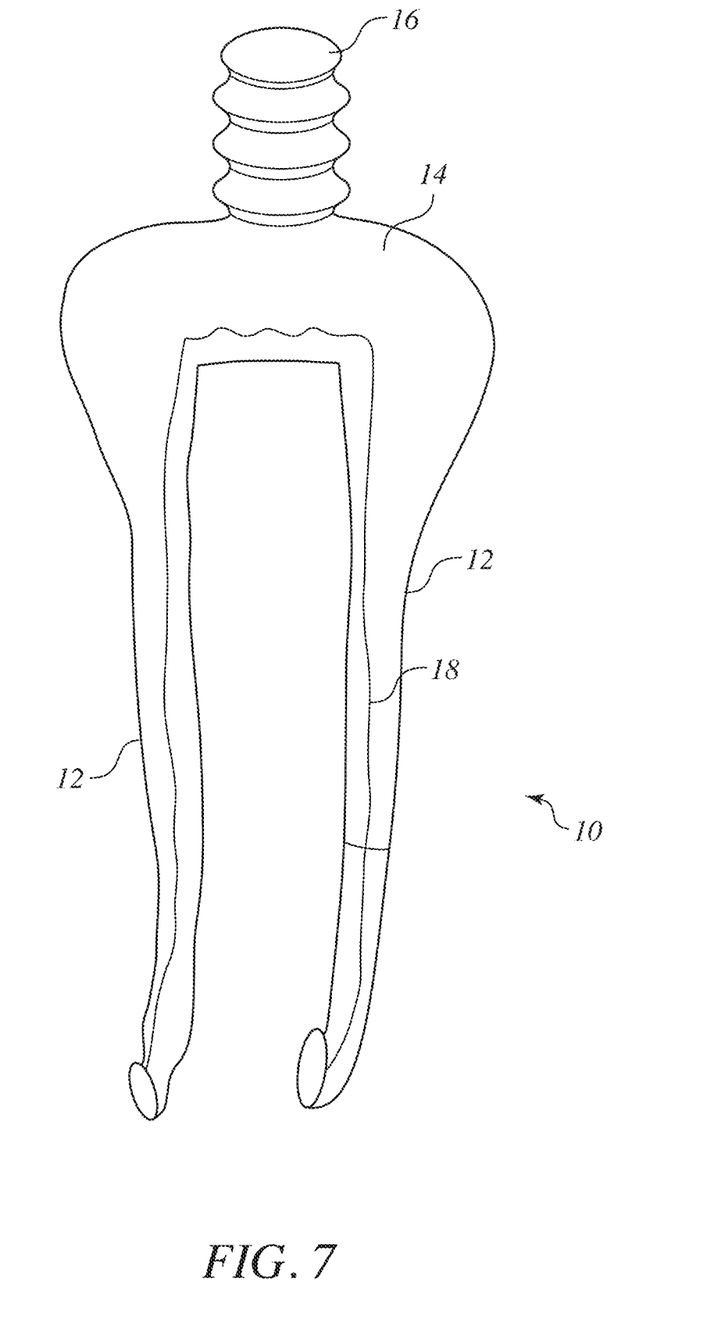
FIG. 7 is a top plan view of a nasal breathing device showing a monolithic construction and long thin legs that extend substantially parallel to each other in accordance with the invention and also having a malleable, uninterrupted wire embedded in an inferior wall of each of the long thin legs and a transverse segment of the nasal breathing device.
Figure 8:
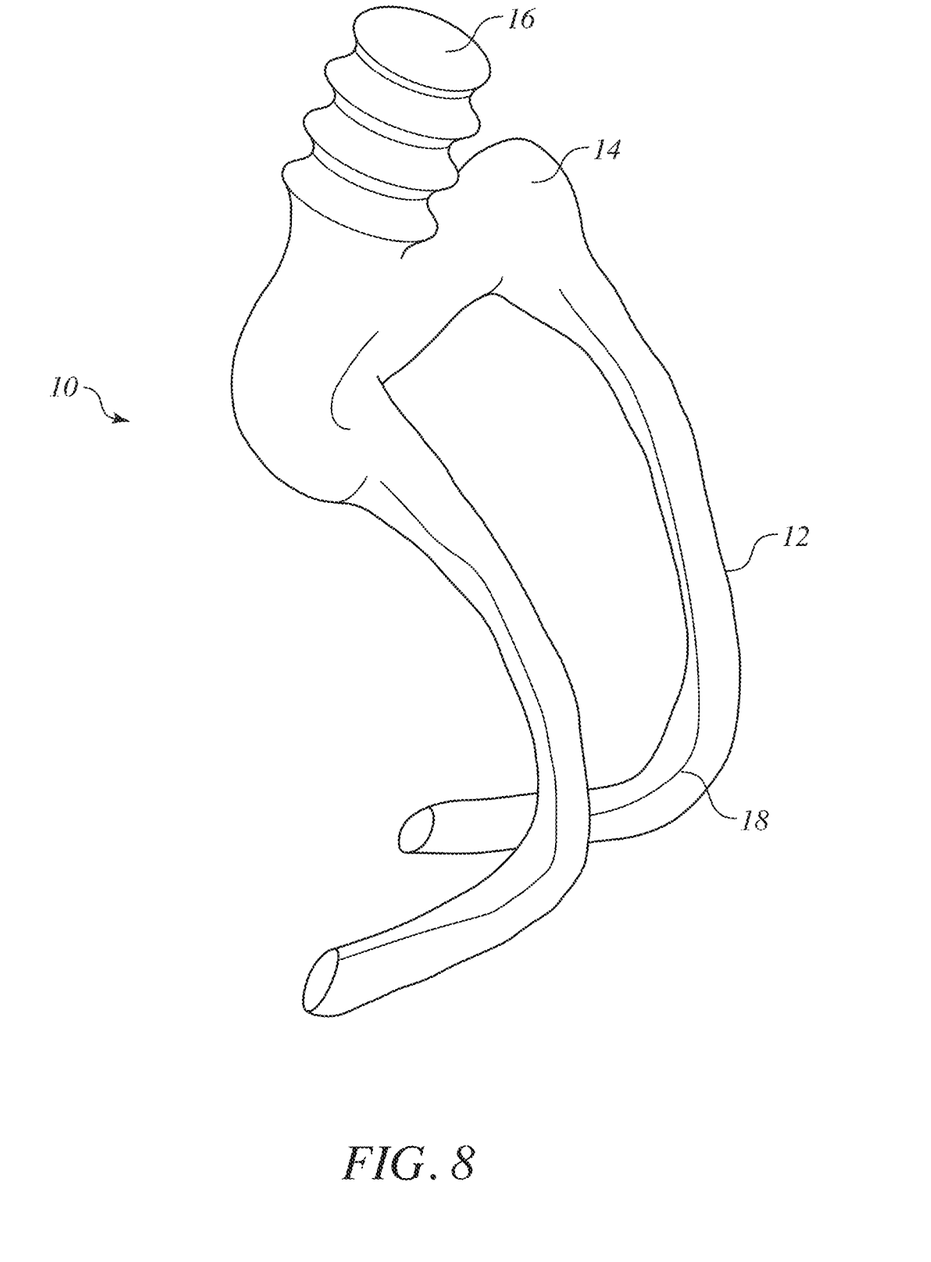
FIG. 8 is a top view of the nasal breathing device with the malleable, uninterrupted wire of FIG. 7, but with the legs shown bent from the parallel orientation of FIG. 8 to have curvature and thereby be able to conform to the floor of the nose.

FIG. 7 and FIG. 8 show a nasal breathing device 10 of the invention having two long thin legs 12 that extend substantially parallel with each from a transverse segment 14. The transverse segment has a centrally located front opening 16. The legs 12 and the transverse segment 14 may be made from a soft, flexible material such as soft polyvinyl chloride (PVC) or neoprene rubber. A malleable, uninterrupted wire 18 is preferably embedded in the inferior wall of the transverse segment 14 and in the legs 12 for the purpose of making the part that gets inserted into the nose malleable, i.e., able to bend to conform the contour of the floor of the nose. However, soft, flexible materials other than a malleable, uninterrupted wire may be used instead to establish needed malleability, such as those materials which have a self-bending characteristic as well as having a malleability characteristic.

Soft PVC is currently used in nasal airway products, such as that manufactured by Rusch that is described as "Sterile, single-use nasopharyngeal airways feature soft PVC and bevel tip with an interior striation for smooth and easy suction and catheter insertion." Neoprene rubber is likewise currently used in nasal airway products, such as CURAPLEX by Tri-anim whose Robertazzi style nasopharyngeal airways product is described as "Curaplex Robertazzi latex free nasopharyngeal airways are made with flexible neoprene. The soft neoprene and blunt tip prevent damage to the nasal passage while resisting collapse or kinking."

The malleable, uninterrupted wire 18 is embedded in the legs 12 and embedded in the transverse segment 14 in a manner that enables the two legs 12 to bend relative to the transverse segment 14. The legs 12 with the embedded malleable wire 18 are movable between a relatively straight orientation, at which the legs 12 are in a substantially straight orientation, and a relatively curved orientation, at which the legs are in a curved orientation. The malleable, uninterrupted wire 18 is configured to retain the legs 12 in the relatively straight orientation in an absence of a manual bending force tending to move the wire out of the relatively straight orientation and configured to retain the legs in the relatively curved orientation in an absence of a manual bending force tending to move the wire out of the relatively curved orientation.

Figure 9:
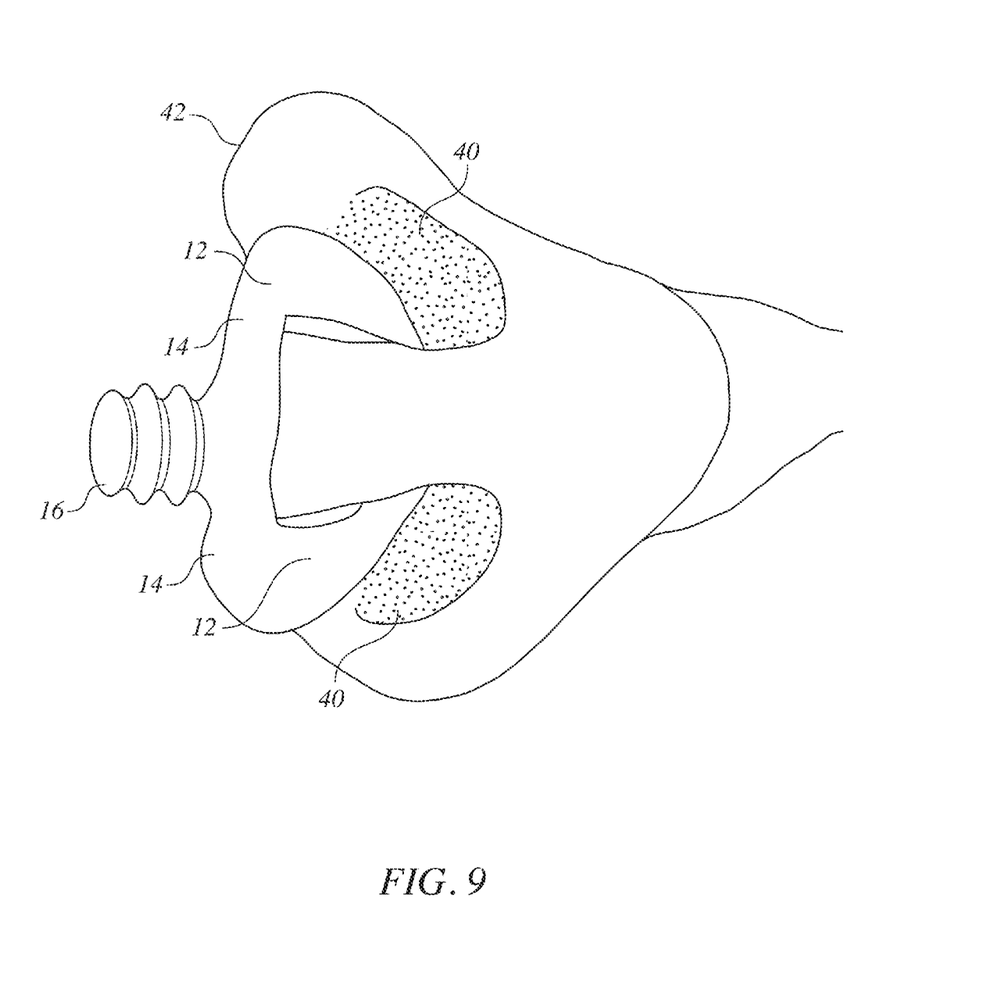
FIG. 9 is a front view of the nasal breathing device of FIG. 7 in position within the nose.

FIG. 9 shows the nasal breathing device 10 in position with the legs 12 inserted into the nasal cavities in the two nostrils 50 of the nose 52. The nasal breathing device 10 has versatility to accept an oxygen cannula for persons who are in need to be connected to a supply of oxygen.

Figure 10:
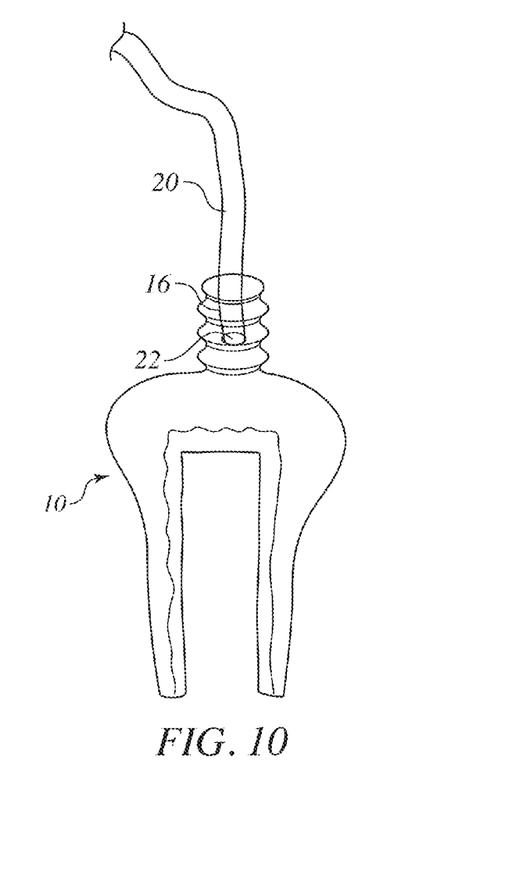
FIG. 10 is a top view of the nasal breathing device of FIG. 7 in combination with a conventional oxygen gas cannula fitted to the nasal breathing device.

FIG. 10 shows a conventional oxygen nasal cannula 20 that is hollow with an open end 22 that fits into the front opening 16 of the nasal breathing device 10 and thus the device 10 accepts the conventional oxygen nasal cannula 20.

Figure 11:
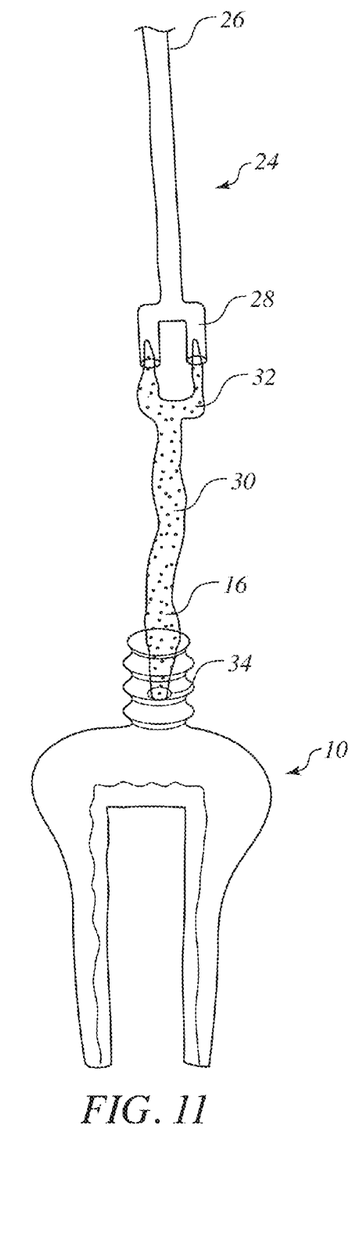
FIG. 11 is a top view of an adaptor between a conventional bi-prong oxygen nasal cannula and the nasal breathing device of FIG. 7 all in a mating relationship with each other.
Figure 12:
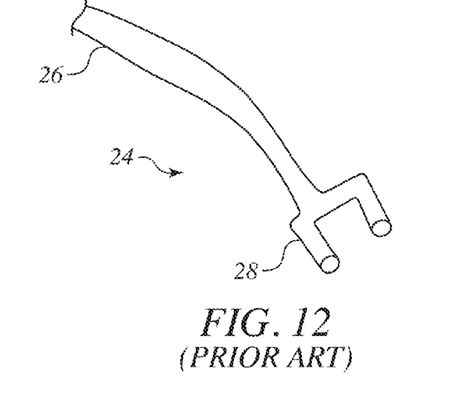
FIG. 12 is a top view of the conventional bi-prong nasal oxygen cannula that is depicted in FIG. 11.

FIG. 11 shows a conventional bi-prong oxygen nasal cannula 24 that is hollow with an open tip 26 at one end and with bi-prongs 28 at the other end. The bi-prongs 28 may be mated with bi-prongs 30 at an end of an adaptor 32. The adaptor 32 is hollow with a further end 34 that is open inserted into the front opening 16 of the nasal breathing device 10. The bi-prongs 28, 30 are open at their respective ends and hollow inside. FIG. 12 shows just the conventional bi-prong oxygen cannula 24.

Figure 13:
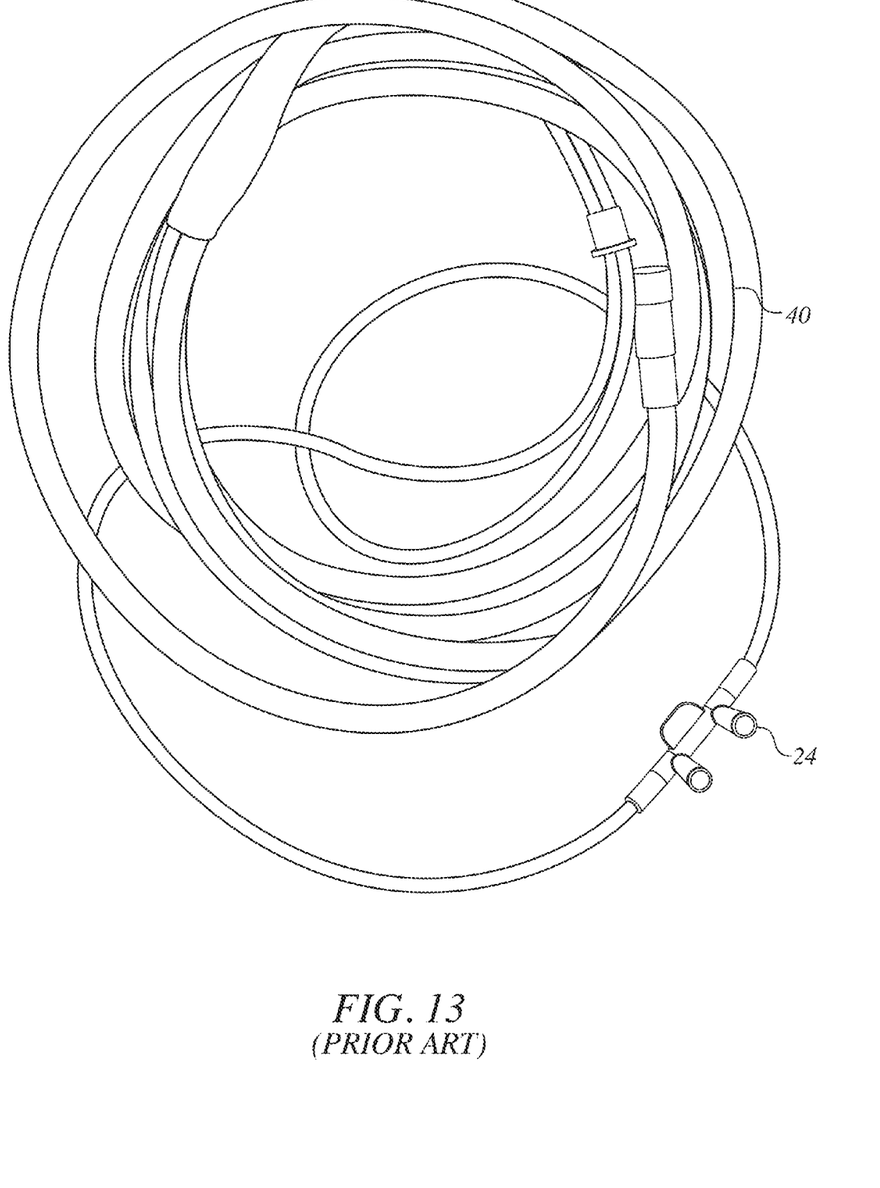
FIG. 13 is a top view of a conventional oxygen nasal cannula with conventional tubing.
Figure 14:
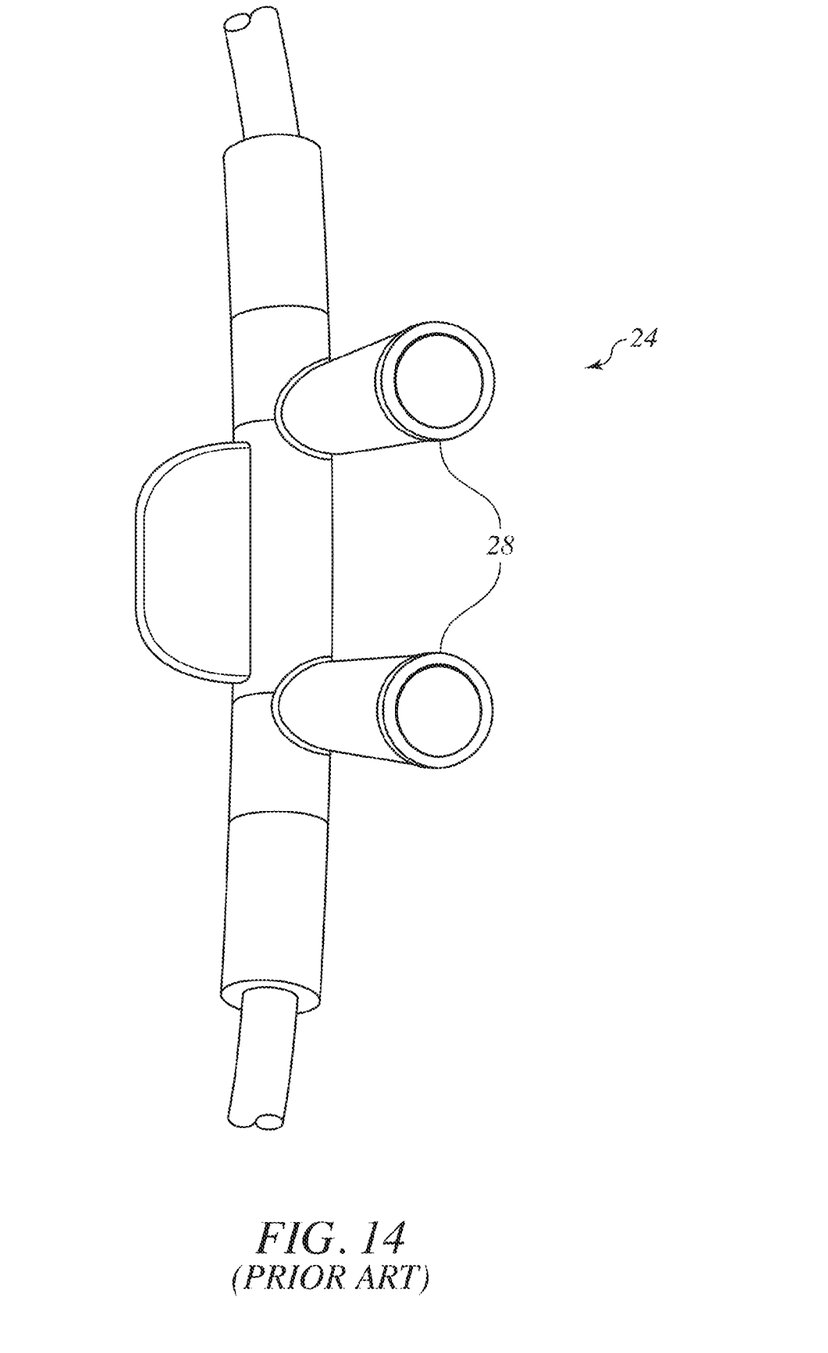
FIG. 14 is a nasal end of the conventional oxygen nasal cannula of FIG. 11 with conventional tubing, with the nasal end to be placed in the nose at both sides of the septum.

FIG. 13 and FIG. 14 illustrate a conventional oxygen nasal cannula 24 with conventional tubing 40. The nasal end of the conventional oxygen nasal cannula 24 is to be placed in the nose at both sides of the septum.

Figure 15:
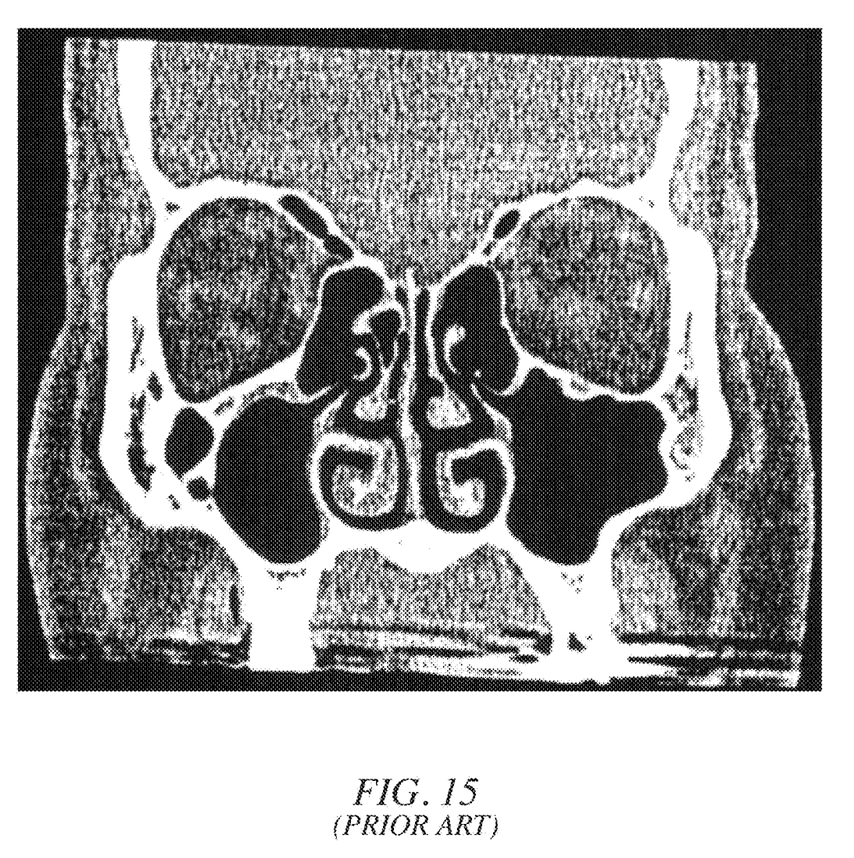
FIG. 15 is a CT scan showing a front view (coronal view) of the upper face.

FIG. 15 shows a conventional CT scan, which is an acronym for computed tomography scan, more commonly known as a CT or CAT scan. The nasal cavities are featured in the center between the orbits and the sinuses. One can appreciate how tight it is within the nasal passages and how little room there is for devices to be emplaced unless they are very thin, such as 3-4 millimeter in diameter. The present invention is configured to taper to become very thin in its tubular shape so as to be comfortably on the floor of the nose.

The CT scan is a conventional diagnostic medical test that, like traditional x-rays, produces multiple images or pictures of the inside of the body. The cross-sectional images generated during a CT scan can be reformatted in multiple planes, and can even generate three-dimensional images. These images can be viewed on a computer monitor, printed on film or transferred to a CD or DVD. CT images typically provide greater detail than traditional x-rays, particularly of soft tissues and blood vessels.

Figure 16:
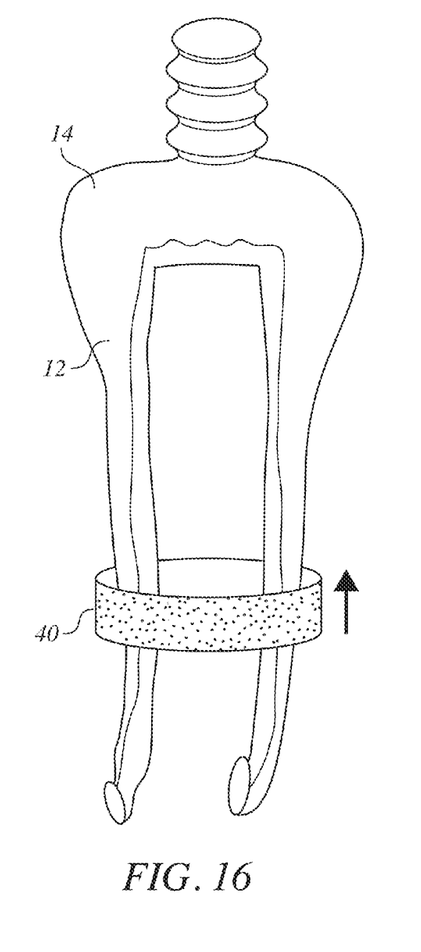
FIG. 16 is a top plan view of a nasal breathing device of FIG. 7 with an encircling band around the legs to keep the distal tubes parallel for ease of insertion into the nose.
Figure 17:
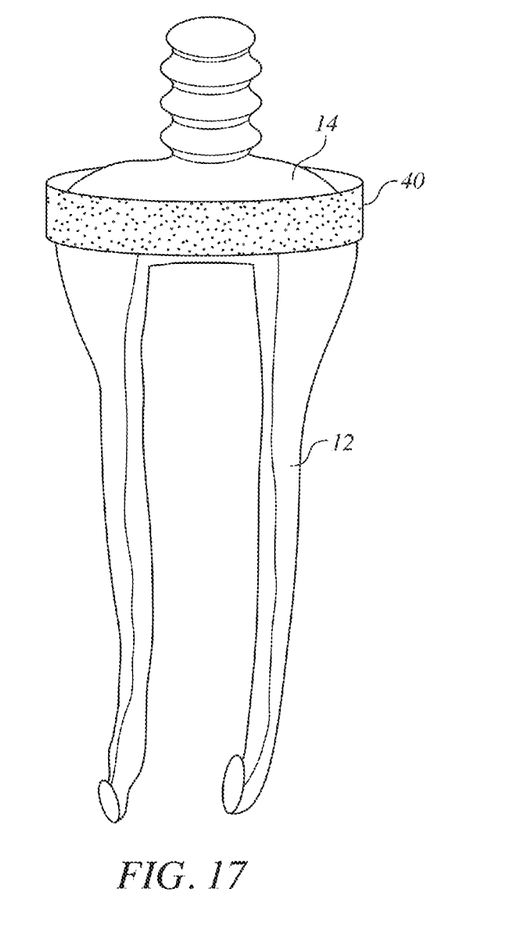
FIG. 17 is a top plan view of a nasal breathing device of FIG. 7 with the encircling band of FIG. 13 shown displaced from the position of FIG. 13.

FIG. 16 and FIG. 17 show an encircling band 44 that starts off around the legs 12 in FIG. 16 (i.e., encircling both of the legs 12) and is loosely fitted. As the legs 12 are inserted into the nostrils, the encircling band 40 rides up to stay outside the nose and is retained at the transverse segment 14 as shown in FIG. 17 (i.e., encircling the transverse segment 14). This is because the band 44 is urged under manual force exerted by the nose to leave the position encircling both of the legs 12 by sliding along the legs until encircling the transverse segment 14.

While the foregoing description and drawings represent the preferred embodiments of the present invention, it will be understood that various changes and modifications may be made without departing from the scope of the present invention.

What is claimed is:

1. A bendable, nasal airway tube device that is positionable to negotiate nasal cavities, comprising:
    a hollow body having two legs that taper and a transverse segment from which extend the two legs, the transverse segment having an opening that accesses the hollow of the hollow body; and
    a malleable wire that is embedded in the two legs and embedded in the transverse segment, the malleable wire being configured to be bendable in response to a manual bending force to enable the two legs to bend relative to the transverse segment between a relatively straight orientation, at which the legs and the malleable wire are in a substantially straight orientation, and a relatively curved orientation, at which the legs and the malleable wire are in a curved orientation, the wire being configured to:
    retain the legs in the relatively straight orientation in an absence of a manual bending force tending to move the malleable wire out of the relatively straight orientation; and
    retain the legs in the relatively curved orientation in an absence of a manual bending force tending to move the malleable wire out of the relatively curved orientation,
    wherein the two legs that taper are configured to negotiate nasal cavities by bending under appropriate manual force to conform to a contour of a floor of the nose so as to be positioned on the floor of the nose.

2. The bendable, nasal airway tube device of claim 1, further comprising:
    a cannula that is hollow with an open end, the open end of the cannula and the opening in the transverse segment being fitted one into the other.

3. The bendable, nasal airway tube device of claim 1, further comprising:
    a hollow adaptor that is elongated with an open end and with bi-prongs at a further end, the open end of the hollow adaptor being compatible with the opening of the hollow body to fit one inside the other, the bi-prongs being compatible with bi-prongs of a bi-prong oxygen nasal cannula to form a mating relationship therewith.

4. The bendable, nasal airway tube device of claim 1, further comprising:
    a band that is movable by sliding along the legs between a position that encircles both of the legs to keep the legs parallel and a position that encircles the transverse segment.

5. A method of positioning a bendable, nasal airway tube device to negotiate nasal cavities, comprising:
    bending malleable wire and two legs relative to a transverse segment of a hollow body between a relatively straight orientation, at which the legs and the wire are in a substantially straight orientation, and a relatively curved orientation, at which the legs and the wire are in a curved orientation, the malleable wire being embedded in the legs and in the transverse segment, the two legs tapering and extending from the transverse segment and having an opening to access the hollow of the hollow body, the wire retaining the legs:
    in the relatively straight orientation in an absence of a manual bending force tending to move the malleable wire out of the relatively straight orientation; and
    in the relatively curved orientation in an absence of a manual bending force tending to move the malleable wire out of the relatively curved orientation; and
    negotiating the two legs that taper within nasal cavities by bending under appropriate manual force to conform to a contour of a floor of the nose and so as to be positioned on the floor of the nose.

6. The method of claim 5, further comprising:
fitting an open end of a hollow cannula and the opening in the transverse segment one into the other.

7. The method of claim 5, further comprising:
fitting an open end of a hollow adaptor and an opening of a hollow body one inside the other, the hollow adaptor being elongated with the open end and with bi-prongs at a further end, the bi-prongs being compatible with bi-prongs of a bi-prong oxygen nasal cannula to form a mating relationship therewith.

8. The method of claim 5, further comprising:
moving a band between a position that encircles both of the legs to a position that encircles the transverse segment.

9. The bendable, nasal airway tube device of claim 1, wherein the transverse segment is made from a flexible material selected from the group consisting of polyvinyl chloride and neoprene rubber.

10. The bendable, nasal airway tube device of claim 1, wherein the transverse segment includes a connecting portion that extends between proximal ends of the two legs and a ribbed portion that extends centrally from the connecting portion to the opening, the ribbed portion having a contour with a plurality of successive peak and valley formations.

11. The bendable, nasal airway tube device of claim 1, wherein the legs taper to have a diameter of 4 millimeters.

12. The bendable, nasal airway tube device of claim 1, wherein the legs taper to have a diameter of 3 millimeters.

* * * * *